(12) United States Patent
Kobayashi (10) Patent No.: US 11,418,772 B2
(45) Date of Patent: Aug. 16, 2022

(54) IMAGING DEVICE BALANCING DEPTH OF FIELD AND RESOLUTION

(71) Applicant: Sony Olympus Medical Solutions Inc., Tokyo (JP)

(72) Inventor: Motoaki Kobayashi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/766,294

(22) PCT Filed: Nov. 27, 2018

(86) PCT No.: PCT/JP2018/043602
§ 371 (c)(1),
(2) Date: May 22, 2020

(87) PCT Pub. No.: WO2019/107359
PCT Pub. Date: Jun. 6, 2019

(65) Prior Publication Data
US 2021/0281820 A1   Sep. 9, 2021

(30) Foreign Application Priority Data
Nov. 29, 2017   (JP) .............................. JP2017-229614

(51) Int. Cl.
*G06T 7/11* (2017.01)
*H04N 13/296* (2018.01)
(Continued)

(52) U.S. Cl.
CPC ....... *H04N 13/296* (2018.05); *A61B 1/00188* (2013.01); *A61B 1/053* (2013.01);
(Continued)

(58) Field of Classification Search
CPC .............. H04N 13/296; H04N 13/239; H04N 5/232125; H04N 2005/2255;
(Continued)

(56) References Cited

U.S. PATENT DOCUMENTS

2017/0358094 A1* 12/2017 Sun ..................... G06T 7/174
2018/0077404 A1*  3/2018 Bechtel ............... H04N 5/2254
(Continued)

FOREIGN PATENT DOCUMENTS

| JP | 06-059196 A | 3/1994 |
| JP | 2012-027263 A | 2/2012 |
| WO | 2013/031512 A1 | 3/2013 |

OTHER PUBLICATIONS

International Search Report and Written Opinion dated Mar. 5, 2019 for PCT/JP2018/043602 filed on Nov. 27, 2018, 8 pages including English Translation of the International Search Report.

*Primary Examiner* — Patrick E Demosky
(74) *Attorney, Agent, or Firm* — Xsensus LLP (57) ABSTRACT

An imaging device according to the present invention includes: first and second image sensors that respectively capture a first optical image and a second optical image having parallax with each other; a first imaging optical system that forms the first optical image on a light receiving surface of the first image sensor; and a second imaging optical system that forms the second optical image on a light receiving surface of the second image sensor. Each of focal positions of the first imaging optical system and the second imaging optical system is deviated along an optical axis direction and is positioned within mutual depth of field.

11 Claims, 6 Drawing Sheets

(51) Int. Cl.
| | |
|---|---|
| *H04N 13/239* | (2018.01) |
| *H04N 5/232* | (2006.01) |
| *A61B 1/00* | (2006.01) |
| *A61B 1/05* | (2006.01) |
| *G02B 7/09* | (2021.01) |
| *G02B 7/28* | (2021.01) |
| *G02B 21/00* | (2006.01) |
| *G02B 21/24* | (2006.01) |
| *G02B 21/36* | (2006.01) |
| *H04N 5/225* | (2006.01) |

(52) U.S. Cl.
CPC ............... *G02B 7/09* (2013.01); *G02B 7/28* (2013.01); *G02B 21/0012* (2013.01); *G02B 21/241* (2013.01); *G02B 21/365* (2013.01); *H04N 5/232125* (2018.08); *H04N 13/239* (2018.05); *H04N 2005/2255* (2013.01)

(58) Field of Classification Search
CPC ...... A61B 1/00188; A61B 1/053; G02B 7/09; G02B 7/28; G02B 21/0012; G02B 21/241; G02B 21/365; G02B 23/2415; G06T 7/11; G06T 7/174; G06T 7/194; G06T 2207/20028; G06T 2207/10148
See application file for complete search history.

(56) References Cited

U.S. PATENT DOCUMENTS

2019/0050998 A1\* 2/2019 Kirby ...................... G06T 7/579
2019/0200847 A1\* 7/2019 Uchida .............. A61B 1/00193

\* cited by examiner

IMAGING DEVICE BALANCING DEPTH OF FIELD AND RESOLUTION

CROSS-REFERENCE TO RELATED APPLICATIONS

The present application is based on PCT filing PCT/JP2018/043602, filed Nov. 27, 2018, which claims priority to JP 2017-229614, filed Nov. 29, 2017, the entire contents of each are incorporated herein by reference.

TECHNICAL FIELD

The present invention relates to an imaging device.

BACKGROUND ART

In medical endoscope systems, there is an increasing demand for stereoscopic observation.

Conventionally, various types of endoscope systems for stereoscopic vision have been known. For example, Patent Literature 1 discloses an endoscope system for stereoscopic vision which includes a rigid endoscope having optical systems for the left and right eyes and two imaging units that respectively image a left-eye image signal and a right-eye image signal based on light condensed by each optical system.

CITATION LIST

Patent Literature

Patent Literature 1: WO 2013/031512

DISCLOSURE OF INVENTION

Technical Problem

In recent years, in order to improve image quality, the number of pixels of image sensors has been increased. When improving the image quality, generally, a diaphragm diameter is increased to secure the resolution of an image. As the diaphragm diameter increases, the depth of field decreases, and as a result, the focusing range in the image decreases. As described above, when improving the image quality and trying to improve the resolution, there is a trade-off relationship that the depth of field decreases. Given the trade-off relationship described above, there is a need for a technique that can suppress the decrease of the depth of field even when the resolution is increased.

The present invention has been made in view of the above, and an object of the present invention is to provide an imaging device capable of suppressing a decrease in a depth of field even when a resolution is increased.

To solve the above-described problem and achieve the object, an imaging device according to the present invention includes: first and second image sensors that respectively capture a first optical image and a second optical image having parallax with each other; a first imaging optical system that forms the first optical image on a light receiving surface of the first image sensor; and a second imaging optical system that forms the second optical image on a light receiving surface of the second image sensor, wherein each of focal positions of the first imaging optical system and the second imaging optical system is deviated along an optical axis direction and is positioned within mutual depth of field.

Moreover, the above-described imaging device according to the present invention further includes a focus processing unit that adjusts the focal positions of the first and second imaging optical systems with a constant deviation amount.

Moreover, the above-described imaging device according to the present invention further includes a focus processing unit that adjusts the focal positions of the first and second imaging optical systems so that a deviation amount on a closer point side in the optical axis direction is larger than the deviation amount on a far point side.

Moreover, in the above-described imaging device according to the present invention, the focus processing unit determines the focus position based on an image captured by the first or second image sensor.

Moreover, in the above-described imaging device according to the present invention, the imaging device is mounted on a medical endoscope or a surgical microscope.

Advantageous Effects of Invention

According to this invention, an effect is exhibited in which the decrease in the depth of field can be suppressed even when the resolution is increased.

BEST MODE FOR CARRYING OUT THE INVENTION

Hereinafter, embodiments for carrying out the present invention (hereinafter referred to as "embodiments") will be described with reference to the accompanying drawings. In the description of the drawings, the same portions are denoted by the same reference numerals. In addition, the drawings are schematic, and the dimensions of the same portion, the size ratio between the same portions, and the like may be different between the drawings.

First Embodiment

Figure 1:
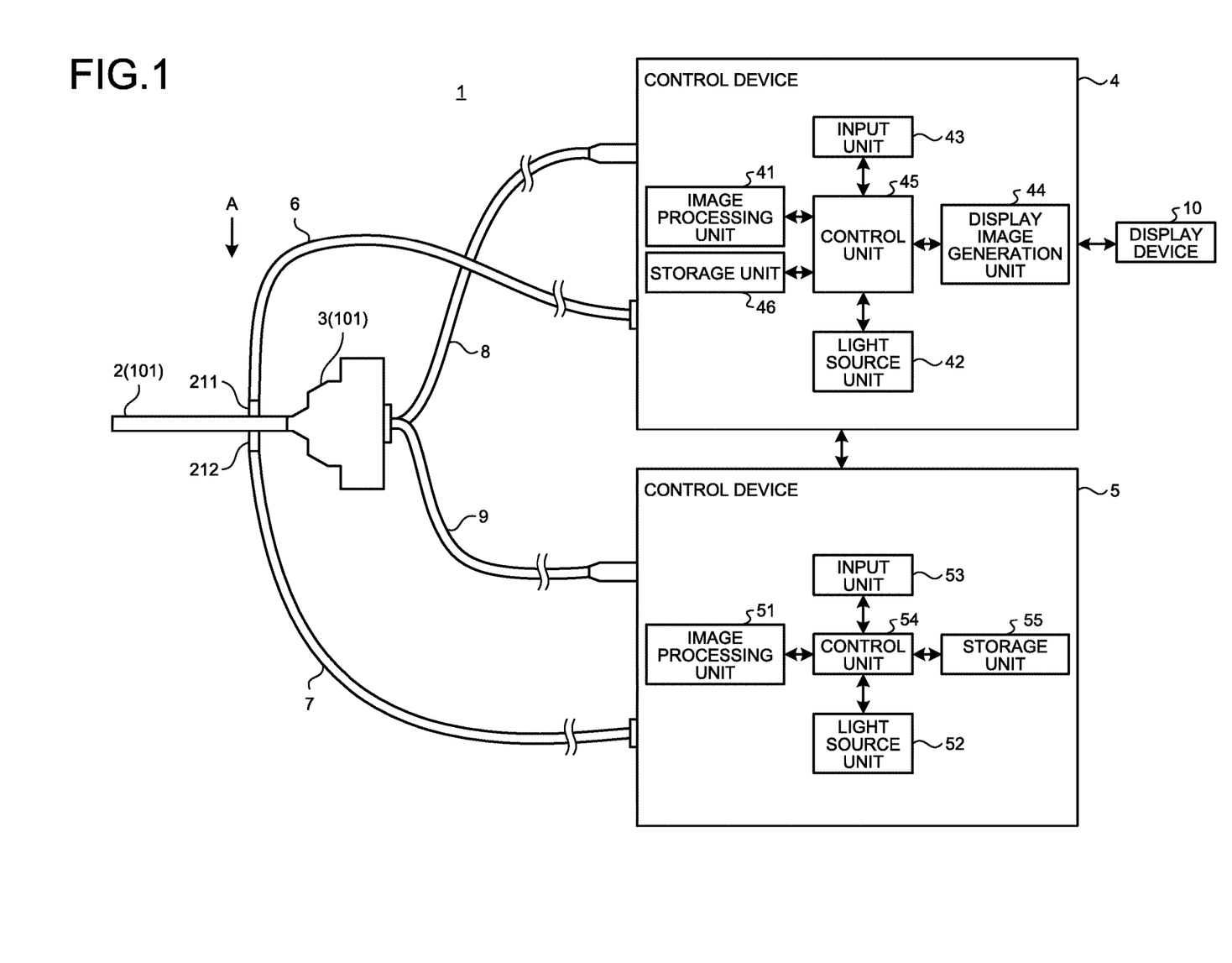
FIG. 1 is a diagram illustrating a schematic configuration of a medical endoscope system according to a first embodiment of the present invention.

FIG. 1 is a diagram illustrating a schematic configuration of a medical endoscope system according to a first embodiment of the present invention. A medical endoscope system 1 illustrated in FIG. 1 is a system for stereoscopically observing the inside of a living body. The medical endoscope system 1 includes a rigid endoscope 2 of which a distal end portion is inserted into the living body and which condenses light in the living body and illuminates the living body, a camera head 3 which images the light from the living body condensed by the rigid endoscope 2 and generates two image signals having parallax with each other, a control device (first control device) 4 which controls the operation of the camera head 3 and generates first illumination light to be supplied to the rigid endoscope 2, a control device (second control device) 5 which controls the operation of the camera head 3 and generates second illumination light to be supplied to the rigid endoscope 2, a light guide cable (first light guide cable) 6 which connects the rigid endoscope 2 and the control device 4 and transmits the first illumination light, a light guide cable (second light guide cable) 7 which connects the rigid endoscope 2 and the control device 5 and transmits the second illumination light, two transmission cables 8 and 9 which respectively connect the camera head 3 with the control devices 4 and 5 and transmit electric signals and the like, and a display device 10 which is connected to the control device 4 and displays information such as images. The rigid endoscope 2 and the camera head 3 configure an imaging device 101.

Figure 2:
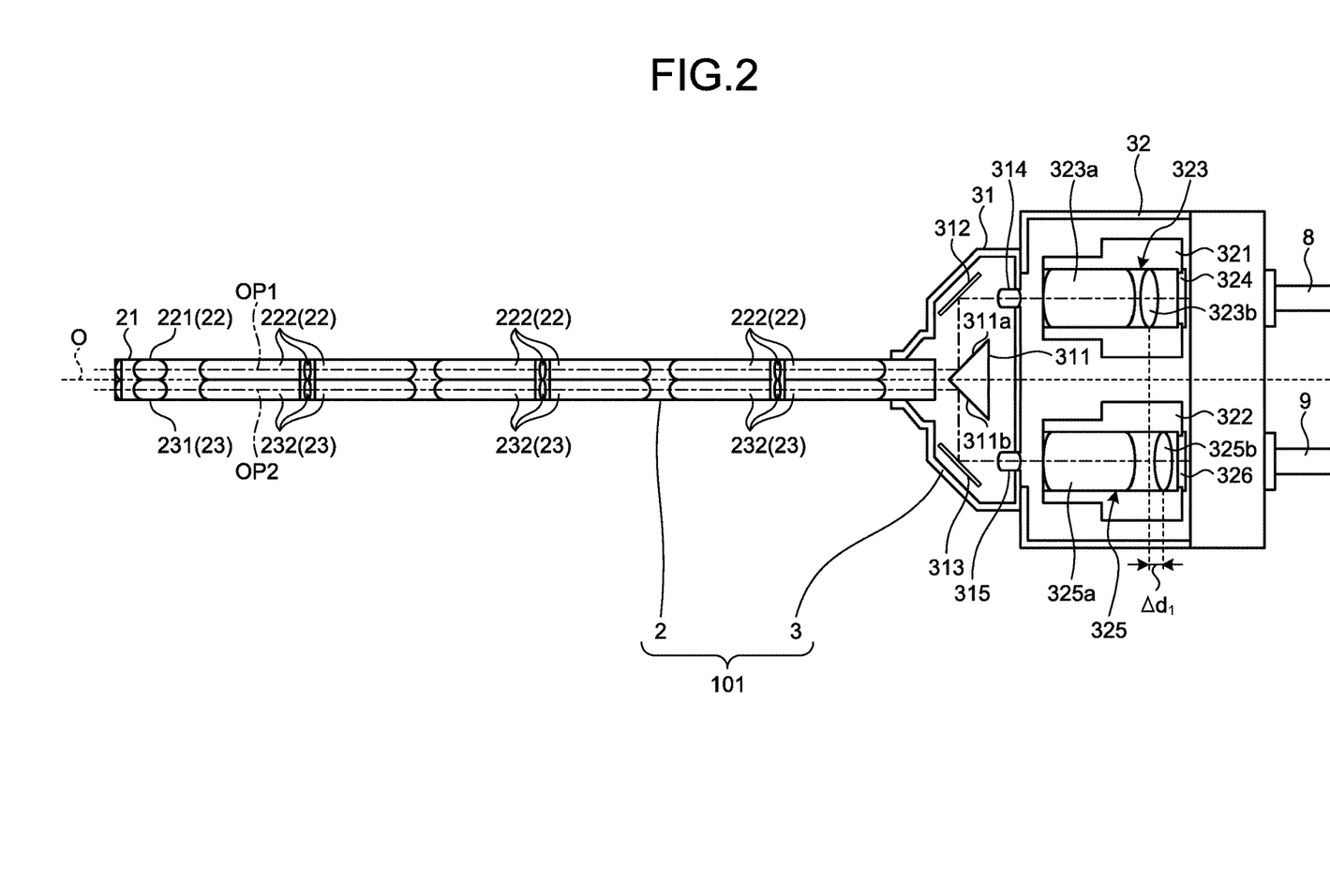
FIG. 2 is a diagram illustrating an internal configuration of a rigid endoscope and a camera head included in the medical endoscope system according to the first embodiment of the present invention.

FIG. 2 is a diagram illustrating the internal configuration of the rigid endoscope 2 and the camera head 3 and is a diagram illustrating the internal configuration of the rigid endoscope 2 and the camera head 3 in the direction of arrow A in FIG. 1. First, the configuration of the rigid endoscope 2 will be described. The rigid endoscope 2 includes an insertion tube 21 having a hard and elongated shape, a first condensing optical system 22 and a second condensing optical system 23 arranged side by side inside the insertion tube 21, and a first illumination optical system and a second illumination optical system (not illustrated) which propagate illumination light from respective light sources of the control devices 4 and 5 to irradiate a living body. The rigid endoscope 2 is detachably and non-rotatably connected to the camera head 3.

A first mounting portion 211 for mounting the distal end portion of the light guide cable 6 and a second mounting portion 212 for mounting the distal end portion of the light guide cable 7 are provided at radially opposed positions on the outer peripheral portion of the insertion tube 21. The first mounting portion 211 and the second mounting portion 212 are connected to the first illumination optical system and the second illumination optical system inside the insertion tube 21, respectively.

The first condensing optical system 22 includes a first objective optical system 221 and a first relay optical system 222 in this order from the distal end side of the insertion tube 21. The first objective optical system 221 is provided at the distal end portion of the insertion tube 21, and focuses first observation light from an observed region in a living body. The first relay optical system 222 guides the first observation light condensed by the first objective optical system 221 to the proximal end (the right end in FIG. 2) of the insertion tube 21. The first observation light is emitted from the proximal end of the insertion tube 21 to the camera head 3.

Similarly to the first condensing optical system 22, the second condensing optical system 23 includes a second objective optical system 231 and a second relay optical system 232 in order from the distal end side. Second observation light condensed by the second condensing optical system 23 is emitted from the proximal end of the insertion tube 21 to the camera head 3. The second condensing optical system 23 is spaced apart from the first condensing optical system 22 in the radial direction of the insertion tube 21 inside the insertion tube 21. An optical axis OP2 of the second condensing optical system 23 is positioned symmetrically with an optical axis OP1 of the first condensing optical system 22 with respect to a central axis O of the insertion tube 21.

The first illumination optical system is connected to the first mounting portion 211 and includes a light guide that propagates the first illumination light from the light guide cable 6 and a first illumination lens that emits the first illumination light from the light guide to the outside of the insertion tube 21. Similarly, the second illumination optical system is connected to the second mounting portion 212 and includes a light guide that propagates the second illumination light from the light guide cable 7 and a second illumination lens that emits the second illumination light from the light guide to the outside of the insertion tube 21.

Next, the configuration of the camera head 3 will be described with reference to FIG. 2. The camera head 3 includes an optical path separation unit 31 which separates the optical path of the first observation light from the first condensing optical system 22 and the optical path of the second observation light from the second condensing optical system 23 and an imaging unit 32 which captures the first and second observation lights to generates two image signals.

The optical path separation unit 31 includes a triangular prism 311 which reflects the first and second observation lights to change the optical paths thereof in the direction opposite to each other, a pair of mirrors 312 and 313 which respectively reflect the first and second observation lights reflected by the triangular prism 311 to make the optical paths thereof parallel to each other, and a pair of eyepiece optical systems 314 and 315 which emit the first and second observation lights reflected by the mirrors 312 and 313 to the imaging unit 32, respectively.

The triangular prism 311 has a triangular prism shape of which the bottom surface is a right-angled isosceles triangle. A first side surface 311a and a second side surface 311b which have the same area and are orthogonal to each other are arranged at 45 degrees with the optical axis OP1 of the first condensing optical system 22 and the optical axis OP2 of the second condensing optical system 23 in the rigid endoscope 2 mounted on the camera head 3, respectively. The first side surface 311a reflects the first observation light and bends the optical path thereof by 90 degrees to be upward in FIG. 2. The second side surface 311b reflects the second observation light and bends the optical path thereof by 90 degrees to be downward in FIG. 2.

The mirror 312 and the mirror 313 are arranged symmetrically with respect to the central axis O of the insertion tube 21 of the rigid endoscope 2 connected to the camera head 3. The surface of the mirror 312 forms an angle of 45 degrees with the direction in which the first observation light reflected by the first side surface 311a is incident, and reflects the first observation light in a direction parallel to the central axis O. The surface of the mirror 313 forms an angle of 45 degrees with the direction in which the second observation light reflected by the second side surface 311b is incident, and reflects the second observation light in a direction parallel to the central axis O.

The eyepiece optical system 314 and the eyepiece optical system 315 are positioned symmetrically with respect to the central axis of the insertion tube 21. The first observation light reflected by the mirror 312 passes through the eyepiece optical system 314 and enters the imaging unit 32. The second observation light reflected by the mirror 313 passes through the eyepiece optical system 315 and enters the imaging unit 32.

The imaging unit 32 includes a first imaging unit 321 which images the first observation light to generate an image signal (right-eye image signal) and a second imaging unit 322 which images the second observation light to generate an image signal (left-eye image signal).

The first imaging unit 321 includes a first imaging optical system 323 which condenses the first observation light emitted from the eyepiece optical system 314 and a first image sensor 324 which photoelectrically converts the first observation light condensed by the first imaging optical system 323 to generates the right-eye image signal. The first imaging optical system 323 includes a first condensing optical system 323a which condenses the first observation light emitted from the eyepiece optical system 314 and a first tube lens 323b which images the first observation light condensed by the first condensing optical system 323a. The first condensing optical system 323a is configured using one or a plurality of lenses. The first image sensor 324 is configured using an image sensor such as a CCD (Charge Coupled Device) or a CMOS (Complementary Metal Oxide Semiconductor).

The second imaging unit 322 includes a second imaging optical system 325 which condenses the second observation light emitted from the eyepiece optical system 315 and a second image sensor 326 which photoelectrically converts the second observation light condensed by the second imaging optical system 325 to generates the left-eye image signal. The second imaging optical system 325 includes a second condensing optical system 325a which condenses the second observation light emitted from the eyepiece optical system 315 and a second tube lens 325b which images the second observation light condensed by the second condensing optical system 325a. The optical axis of the second imaging optical system 325 is parallel to the optical axis of the first imaging optical system 323. The configurations of the second imaging optical system 325 and the second image sensor 326 are the same as the configurations of the first imaging optical system 323 and the first image sensor 324, respectively. Further, in the first embodiment, the depth of field of the first imaging optical system 323 and the depth of field of the second imaging optical system 325 are a range of depths in an optical axis direction that an observer feels in focus. The depth of field of the first imaging optical system 323 and the depth of field of the second imaging optical system 325 are the same range (length). Here, "same" includes a design error.

Figure 3:
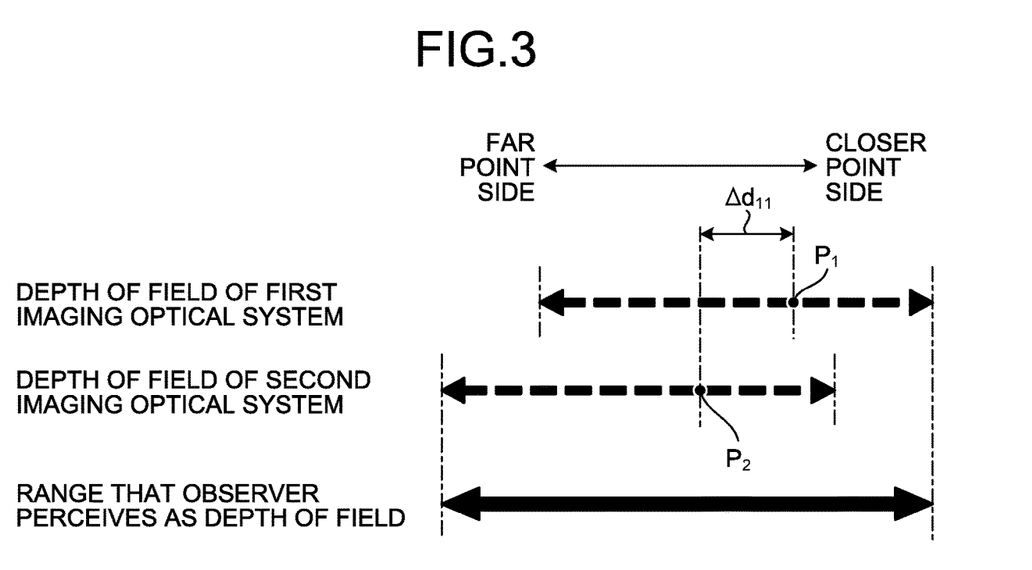
FIG. 3 is a diagram illustrating a depth of field when a focal position of a second imaging optical system is arranged on a far point side from a focal position of a first imaging optical system in the rigid endoscope and the camera head included in the medical endoscope system according to the first embodiment of the present invention.
Figure 4:
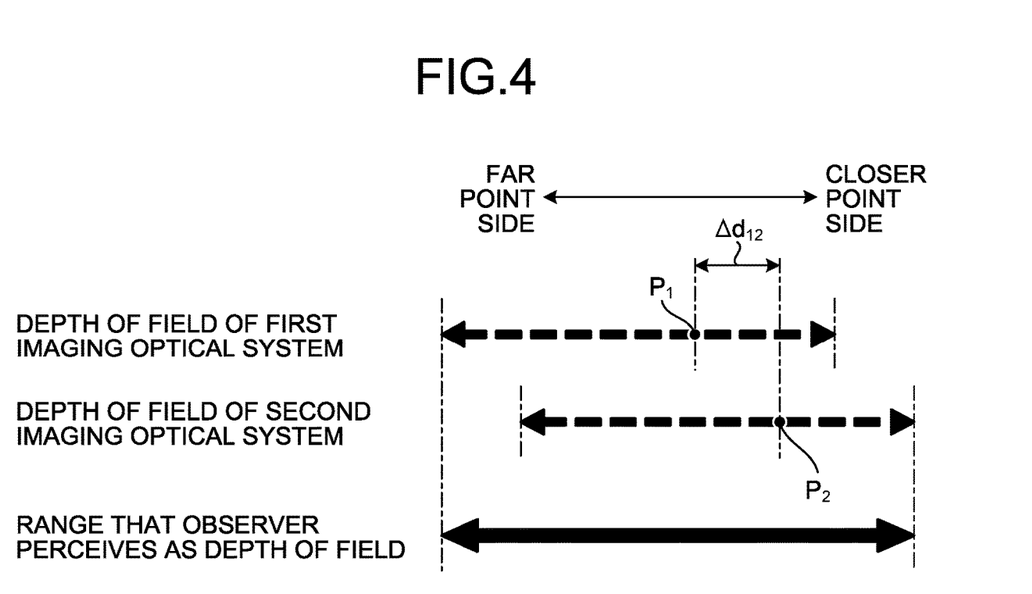
FIG. 4 is a diagram illustrating a depth of field when the focal position of the second imaging optical system is arranged on a closer point side than the focal position of the first imaging optical system in the rigid endoscope and the camera head included in the medical endoscope system according to the first embodiment of the present invention.

Here, the depth of field of the rigid endoscope 2 and the camera head 3 will be described with reference to FIGS. 3 and 4. FIG. 3 is a diagram illustrating a depth of field when a focal position of the second imaging optical system 325 is arranged on a far point side from a focal position of the first imaging optical system 323 in the rigid endoscope 2 and the camera head 3 included in the medical endoscope system 1 according to the first embodiment of the present invention. FIG. 4 is a diagram illustrating a depth of field when the focal position of the second imaging optical system 325 is arranged on a closer point side than the focal position of the first imaging optical system 323 in the camera head 3 included in the medical endoscope system 1 according to the first embodiment of the present invention. In this specification, the "closer point side" refers to a side approaching the imaging optical system (objective lens), and the "far point side" refers to a side away from the imaging optical system.

In the first embodiment, the first tube lens 323b and the second tube lens 325b are different from each other in the positions arranged along the central axis O. Specifically, as illustrated in FIG. 2, the first tube lens 323b and the second tube lens 325b are arranged to be deviated by $\Delta d_1$ along the central axis O (the optical axes OP1 and OP2). For this reason, the focal position $P_1$ of the first imaging optical system 323 is deviated from the focal position $P_2$ of the second imaging optical system 325 in the direction along the central axis O, and further, the ends on the far point side and the ends on the closer point side in the depth of field in both are deviated, respectively. At this time, the deviation amount ($\Delta d_{11}$ and $\Delta d_{12}$ described later) is a value of the range where the focus of the first imaging optical system 323 and the focus of the second imaging optical system 325 are positioned within the range of the depth of field of the opposite imaging optical system.

Here, when the focal position $P_2$ of the second imaging optical system 325 is arranged on the far point side by the deviation amount $\Delta d_{11}$ from the focal position $P_1$ of the first imaging optical system 323, as illustrated in FIG. 3, the range that the observer perceives as the depth of field is from the end on the closer point side in in the depth of field of the first imaging optical system 323 to the end on the far point side in the depth of field of the second imaging optical system 325.

When the focal position $P_2$ of the second imaging optical system 325 is arranged on the closer point side by the deviation amount $\Delta d_{12}$ from the focal position $P_1$ of the first imaging optical system 323, as illustrated in FIG. 4, the range that the observer perceives as the depth of field is from the end on the closer point side in in the depth of field of the second imaging optical system 325 to the end on the far point side in the depth of field of the first imaging optical system 323.

As described above, when the focal position of the two imaging optical systems is deviated along the central axis O, the depth of field of each optical system is deviated so that the depth of field can be apparently deeper than that of the first imaging optical system 323 (or the second imaging optical system 325). Accordingly, even when the diaphragm diameter is increased for higher image quality, and as a result, the depth of field becomes smaller, if the focal position is deviated, the depth of field is deviated, and the decrease in the apparent depth of field can be suppressed.

Next, the configurations of the control devices 4 and 5 will be described with reference to FIG. 1. In the first embodiment, the control device 4 and the control device 5 have a master-slave relationship and perform control in synchronization. The control device 4 that is a master receives the left-eye image signal generated by the second imaging unit 322 from the control device 5 that is a slave and generates a display image signal (three-dimensional image signal) together with the right-eye image signal received from the first imaging unit 321 to output the image signal to the display device 10.

The control device 4 includes an image processing unit 41 which performs predetermined image processing on an image signal generated by the first imaging unit 321, a light source unit (first light source unit) 42 which generates first illumination light and supplies the first illumination light to the light guide cable 6, an input unit 43 which receives inputs of various operation signals, a display image generation unit 44 which generates a display image signal to be displayed on the display device 10, a control unit 45 which controls the operation of the medical endoscope system 1 including the control device 4, and a storage unit 46 which stores various information. The control device 4 is connected to the control device 5 via a transmission cable, receives various information including an image signal from the control device 5, and transmits various control signals and the like to the control device 5. Note that the communication between the control device 4 and the control device 5 may be performed wirelessly.

The image processing unit 41 performs image processing such as synchronization processing, white balance (WB) adjustment processing, gain adjustment processing, gamma correction processing, digital analog (D/A) conversion processing, and format conversion processing on the image signal, and outputs the image signal to the display image generation unit 44.

The light source unit 42 includes a light source configured using an LED (Light Emitting Diode) or a halogen lamp, a light source driver which drives the light source under the control of the control unit 45, and an emission optical system which condenses the light generated by the light source to emit the light to the light guide.

The input unit 43 is a user interface which receives inputs of various operation signals regarding the medical endoscope system 1 including the control device 4.

The display image generation unit 44 generates the three-dimensional image signal corresponding to the display method of the display device 10 as a display image signal by using the right-eye image signal generated by the first imaging unit 321 and the left-eye image signal generated by the second imaging unit 322 and received from the control device 5.

The control unit 45 collectively controls the medical endoscope system 1 by controlling the operation of the camera head 3 or performing control to operate in cooperation with the control device 5 together with controlling the operations of the image processing unit 41, the light source unit 42, and the display image generation unit 44. The control unit 45 adjusts the light amount ratio in the light source unit 42 and the light source unit 52 included in the control device 5 using the brightness information based on the image signal and the brightness information sent from the control device 5 and transmits light source control signals to the light source units 42 and 52, respectively. Further, the control unit 45 generates a clock signal serving as a reference for the operation of each component of the camera head 3 and the control device 5 and a vertical synchronization signal indicating a start timing of each frame of the image signal and outputs the signals to the camera head 3 and each unit of the control device 5.

The storage unit 46 stores various programs for operating the control device 4. The programs include a program for the control device 4 collectively controlling the medical endoscope system 1 as a master. The storage unit 46 is configured using a volatile memory such as a RAM (Random Access Memory) or a nonvolatile memory such as a ROM (Read Only Memory).

In the control device 4 having the above-described functional configuration, the image processing unit 41, the display image generation unit 44, and the control unit 45 are configured using a general-purpose processor such as a CPU (Central Processing Unit) or a dedicated integrated circuit or the like that performs a specific function such as an FPGA (Field Programmable Gate Array).

The control device 5 includes an image processing unit 51, a light source unit (second light source unit) 52, an input unit 53, a control unit 54, and a storage unit 55. Each of these components has the same functional configuration as the corresponding component in the control device 4 described above. However, the control unit 54 performs control for operating the control device 5 as a slave. Further, the storage unit 55 stores a program for operating the control device 5 as a slave.

The light guide cables 6 and 7 are configured by bundling a plurality of optical fibers. In the light guide cable 6, one end is connected to the control device 4, and the other end is mounted on the first mounting portion 211 of the rigid endoscope 2. The first illumination light generated by the control device 4 is guided to the light guide. In the light guide cable 7, one end of is connected to the control device 5, and the other end is mounted on the second mounting portion 212 of the rigid endoscope 2. The second illumination light generated by the control device 5 is guided to the light guide.

The transmission cables 8 and 9 perform communication between the camera head 3 and the control devices 4 and 5, respectively. The transmission cables 8 and 9 are metal cables for transmitting electric signals. Incidentally, the transmission cables 8 and 9 may be fiber cables for transmitting optical signals. In this case, the camera head 3 may be provided with an electro-optical (E/O) conversion function, and each of the control devices 4 and 5 may be provided with a photoelectric (O/E) conversion function. In addition, each of the transmission cables 8 and 9 may be configured by combining the metal cables and the fiber cables, and only image signals may be transmitted by the optical signals, and other signals may be transmitted by the electric signals. Further, the communication between the camera head 3 and the control devices 4 and 5 may be performed wirelessly.

For example, the display device 10 is a three-dimensional display of an integral imaging method using a liquid crystal or an organic EL (Electro Luminescence), a multi-view method, or the like, and a three-dimensional image is displayed based on the three-dimensional image signal generated by the control device 4.

According to the first embodiment of the present invention described above, the focal positions of the two imaging optical systems are deviated along the central axis O so as to increase the apparent depth of field. Therefore, even when the diaphragm diameter is increased for higher image quality, and the depth of field of the optical system itself becomes smaller, it is possible to suppress a decrease in the depth of field that the observer feels in focus.

Second Embodiment

Figure 5:
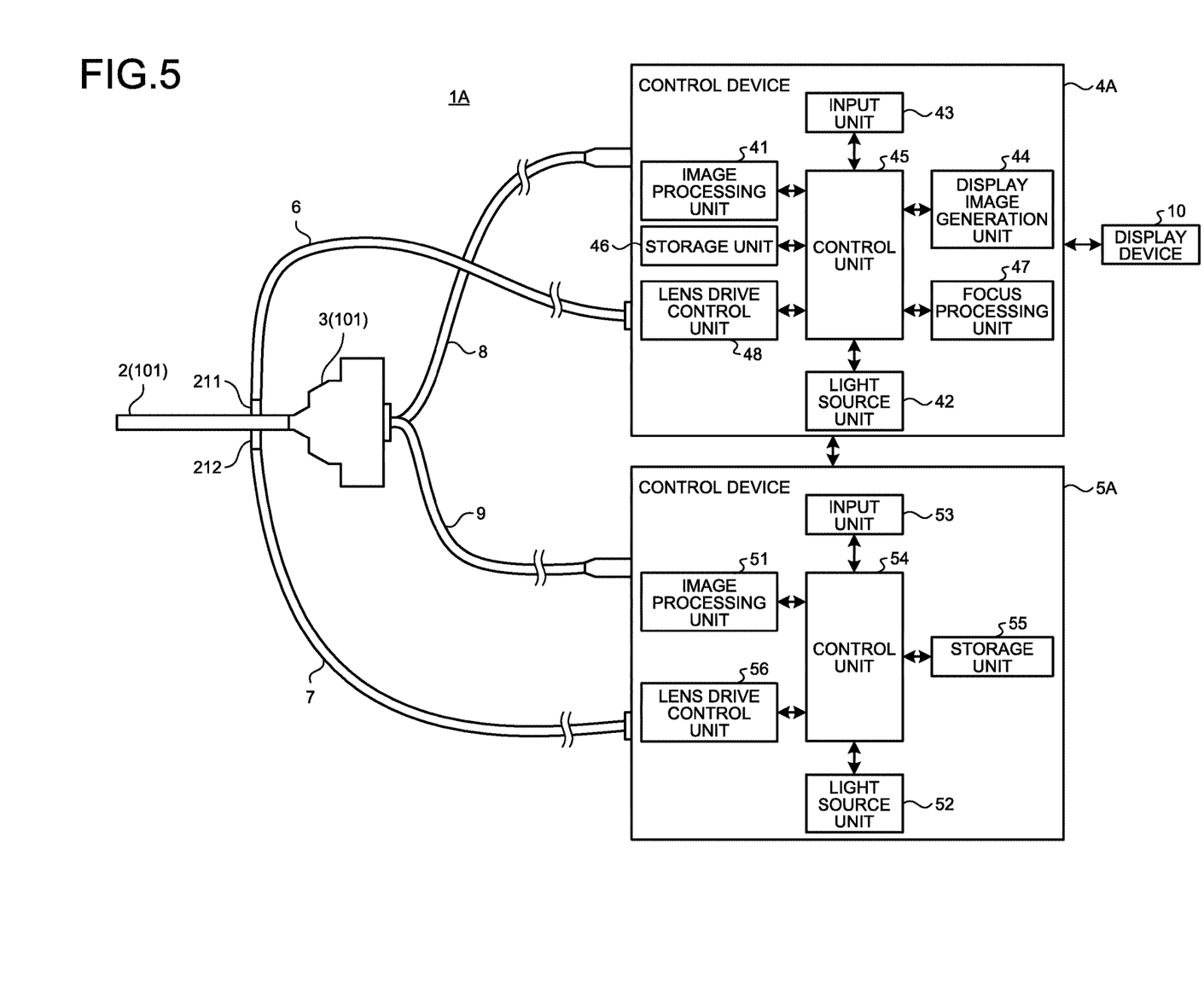
FIG. 5 is a diagram illustrating a schematic configuration of a medical endoscope system according to a second embodiment of the present invention.

Next, a second embodiment of the present invention will be described. FIG. 5 is a diagram illustrating a schematic configuration of a medical endoscope system according to the second embodiment of the present invention. Incidentally, the same components as those described above will be described with the same reference numerals. In the second embodiment, an autofocus function is added to the configuration of the first embodiment.

A medical endoscope system 1A according to the second embodiment includes the rigid endoscope 2 and the camera head 3 described above, the control device (first control device) 4A which controls the operation of the camera head 3 and generates the first illumination light to be supplied to the rigid endoscope, the control device (second control device) 5A which controls the operation of the camera head 3 and generates the second illumination light to be supplied to the rigid endoscope, the light guide cable 6 which connects the rigid endoscope 2 and the control device 4A and transmits the first illumination light, the light guide cable 7 which connects the rigid endoscope 2 and the control device 5A and transmits the second illumination light, two transmission cables 8 and 9 which respectively connect the camera head 3 with the control devices 4A and 5A and transmit electric signals and the like, and the display device 10 which is connected to the control device 4A and displays information such as images.

In the second embodiment, the first tube lens 323b is movable along the optical axis OP1. Similarly, the second tube lens 325b is movable along the optical axis OP2. In the second embodiment, an optical zoom mechanism (not illustrated) for changing the angle of view and a focus mechanism (not illustrated) for changing the focus are driven under the control of the control device 4A, and move the first tube lens 323b. Further, the optical zoom mechanism and the focus mechanism for moving the second tube lens 325b are driven under the control of the control device 5A.

The control device 4A includes the above-described image processing unit 41, light source unit 42, input unit 43, display image generation unit 44, control unit 45, and storage unit 46, a focus processing unit 47, and a lens drive control unit 48.

For example, based on pixel information (luminance signal (Y signal)) for each pixel of a specified area in the entire image of one frame imaged by the first image sensor 324, the focus processing unit 47 detects a contrast and frequency components of the image in the specified area. Then, the focus processing unit 47 calculates a focus evaluation value for evaluating the focus state of the image based on the detected contrast and frequency components. For example, the focus processing unit 47 uses the detected contrast or the sum of the high-frequency components among the frequency components as the focus evaluation value. Incidentally, the focus evaluation value indicates that focusing is higher as the value is the larger.

Then, the focus processing unit 47 operates the first tube lens 323b by the lens drive control unit 48 to sequentially calculate the focus evaluation value while changing the focus position and to sequentially store focus information of the focus position and the focus evaluation value corresponding to the focus position in association with each other in the storage unit 46. Thereafter, the focus processing unit 47 calculates a peak position at which the focus evaluation value becomes the maximum value based on a plurality of pieces of focus information stored in the storage unit 46. In addition, the focus processing unit 47 calculates a moving direction (a direction to a near point or a direction to a far point) and a moving amount for moving the first tube lens 323b to the focus position calculated from the current position of the first tube lens 323b. Then, the focus processing unit 47 outputs a control signal corresponding to the moving direction and the moving amount to the lens drive control unit 48 and the lens drive control unit 56. As described above, in the second embodiment, the focus processing unit 47 executes an AF processing by a so-called hill-climbing method. Note that the above-described AF processing may adopt so-called continuous AF to be always executed or so-called one-touch AF to be executed according to the operation of an operation button (not illustrated) provided on the camera head 3 or the like.

The lens drive control unit 48 moves the first tube lens 323b to a position corresponding to the calculated focus position based on the control signal output from the focus processing unit 47.

The control device 5A includes the above-described image processing unit 51, light source unit 52, input unit 53, control unit 54, storage unit 55, and a lens drive control unit 56.

The lens drive control unit 56 moves the second tube lens 325b to a position corresponding to the calculated focus position based on the control signal output from the focus processing unit 47. Since the first tube lens 323b and the second tube lens 325b have the same moving amount, the deviation amount is constant regardless of autofocus control.

According to the second embodiment of the present invention described above, the effect according to the first embodiment can be obtained even with a configuration in which autofocus is performed.

Incidentally, in the second embodiment described above, the control device 4A executes the autofocus processing based on the image captured by the first image sensor 324. However, the control device 5A may execute the autofocus process based on the image captured by the second image sensor 326, a control device that processes the image captured by the image sensor which receives the light formed by the tube lens which is arranged relatively on the far point side may execute autofocus processing, and conversely, a control device that processes the image captured by the image sensor that receives the light formed by the tube lens arranged on the closer point side may execute the autofocus processing.

Further, in the above-described second embodiment, based on the image captured by the first image sensor 324, the control device 4A executes the autofocus processing of automatically performing the focus adjustment. However, the moving direction and the moving amount of the first tube lens 323b and the second tube lens 325b may be determined based on the moving direction and the moving amount input by the user via the input unit 43. At this time, the focus processing unit 47 maintains the deviation amount of the first tube lens 323b and the second tube lens 325b constant, and determines the moving amount of the first tube lens 323b and the second tube lens 325b according to the input information.

Modification of Second Embodiment

Next, a modification of the second embodiment of the present invention will be described. The configuration of the medical endoscope system according to this modification is the same as the medical endoscope system 1A described above, and thus the description thereof is omitted. Hereinafter, portions different from the second embodiment will be described. In the above-described second embodiment, it is described that the deviation amount between the first tube lens 323b and the second tube lens 325b is constant regardless of the moving direction and the moving amount. In this modification, one tube lens with respect to the other tube lens has a different deviation amount between the case of moving toward the far point side from the reference position and the case of moving toward the closer point side.

Figure 6:
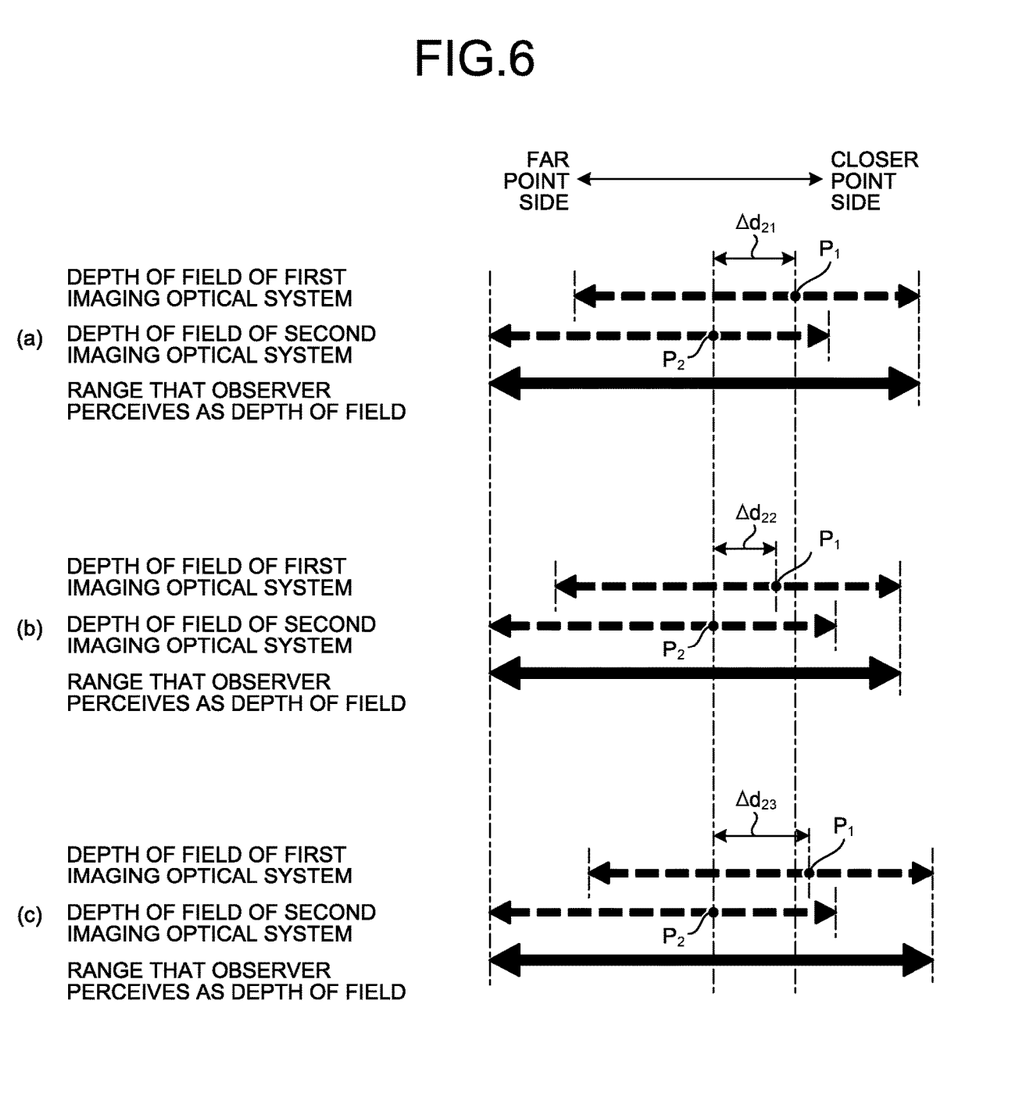
FIG. 6 is a diagram illustrating a depth of field when a focal position of a second imaging optical system 325 with respect to a focal position of a first imaging optical system 323 is moved to a far point side from or a closer point side than a reference position in a rigid endoscope and a camera head included in a medical endoscope system according to a modification of the second embodiment of the present invention.

FIG. 6 is a diagram illustrating a depth of field when the focal position $P_2$ of the second imaging optical system 325 with respect to the focal position $P_1$ of the first imaging optical system 323 is moved to the far point side from or the closer point side than the reference position in the rigid endoscope 2 and the camera head 3 included in the medical endoscope system 1A according to the modification of the second embodiment of the present invention. (a) of FIG. 6 is a diagram illustrating the deviation amount of the focal position when the first tube lens 323b and the second tube lens 325b are arranged at reference positions. (b) of FIG. 6 is a diagram illustrating the deviation amount of the focal position when the first tube lens 323b and the second tube lens 325b are arranged on the far point side from the reference position. (c) of FIG. 6 is a diagram illustrating the deviation amount of the focal position when the first tube lens 323b and the second tube lens 325b are arranged on the closer point side than the reference position.

When the first tube lens 323b and the second tube lens 325b are arranged at reference positions, as illustrated in (a) of FIG. 6, the deviation amount of the focal position of the first imaging optical system 323 and the focal position of the second imaging optical system 325 is set to $\Delta d_{21}$. In this state, when the first tube lens 323b and the second tube lens 325b are moved to the far point side by autofocus, the deviation amounts of the focal position of the first imaging optical system 323 and the focal position of the second imaging optical system 325 when the movement is completed are set to $\Delta d_{22}$ ($<\Delta d_{21}$) (see (b) of FIG. 6).

On the other hand, when the first tube lens 323b and the second tube lens 325b are moved to the closer point side by autofocus, the deviation amounts of the focal position of the first imaging optical system 323 and the focal position of the second imaging optical system 325 when the movement is completed are set to $\Delta d_{23}$ ($>\Delta d_{21}$) (see (c) of FIG. 6).

For the deviation amount from the reference position, for example, information (table or expression) indicating the relationship between the moving direction and the moving amount from the reference position and the deviation amount is stored in the storage unit 46 in advance. When the moving direction and the moving amount of the first tube lens 323b are determined, the focus processing unit 47 extracts the deviation amount corresponding to the moving direction and the moving amount with reference to the storage unit 46 and determines the moving amount of the second tube lens 325b. After that, the lens drive control units 48 and 56 move the first tube lens 323b and the second tube lens 325b in the determined moving direction and moving amount.

As in the modification described above, the deviation amount of the focal position of the first imaging optical system 323 and the focal position of the second imaging optical system 325 may be changed according to the moving direction of the first tube lens 323b and the second tube lens 325b from the reference position.

Third Embodiment

Figure 7:
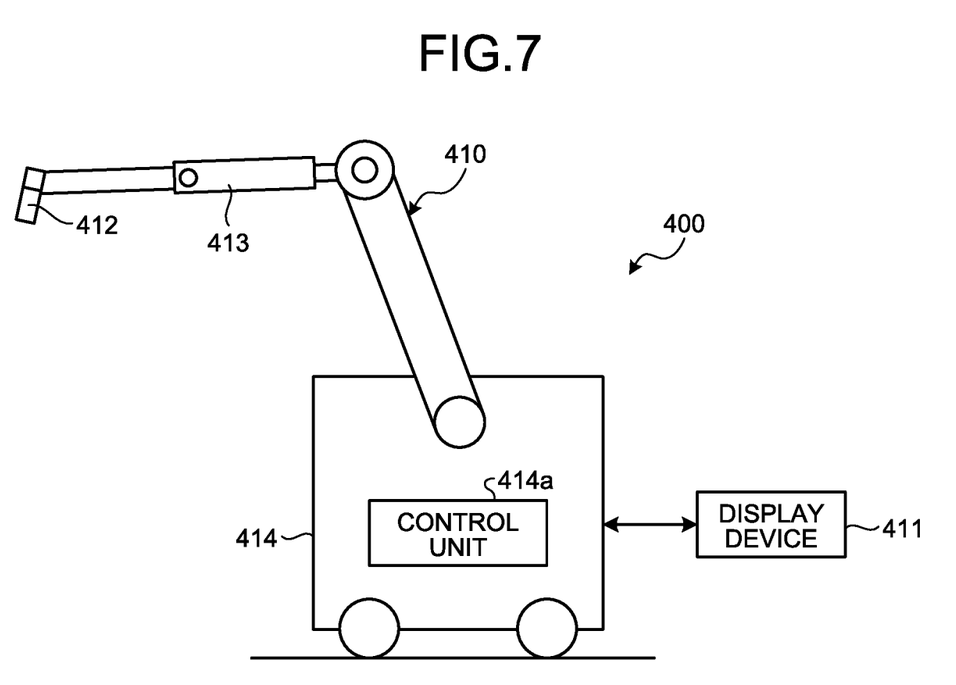
FIG. 7 is a diagram schematically illustrating an overall configuration of a surgical microscope system which is a medical observation system including a medical imaging device according to a third embodiment of the present invention.

Next, a third embodiment of the present invention will be described. FIG. 7 is a diagram schematically illustrating an overall configuration of a surgical microscope system which is a medical observation system including a medical imaging device according to the third embodiment of the present invention. In the above-described first and second embodiments, the rigid endoscope is described as an example. However, in the third embodiment, a surgical microscope system (medical image acquisition system) having a function of enlarging and imaging a predetermined field of view and displaying the captured image is described as an example.

A surgical microscope system 400 includes a microscope device 410 which is a medical imaging device that obtains an image for observing a subject by capturing, and a display device 411 that displays the image captured by the microscope device 410. Note that the display device 411 can be integrally formed with the microscope device 410.

The microscope device 410 includes a microscope unit 412 that enlarges and captures an image of a minute part of the subject, a support unit 413 that includes an arm that is connected to the proximal end portion of the microscope unit 412 and rotatably supports the microscope unit 412, and a base portion 414 that rotatably holds the proximal end portion of the support unit 413 and is movable on a floor surface. The base portion 414 includes a control unit 414a that controls the operation of the surgical microscope system 400. Incidentally, the base portion 414 may be configured to support the support unit 413 by being fixed to a ceiling, a wall surface, or the like, instead of being movably provided on the floor surface. Further, the base portion 414 may include a light source unit that generates illumination light for irradiating the subject from the microscope device 410.

For example, the microscope unit 412 has a column shape, and includes therein the above-described first condensing optical system 22, second condensing optical system 23, optical path separation unit 31, and imaging unit 32. A switch for receiving an input of an operation instruction of the microscope device 410 is provided on the side surface of the microscope unit 412. A cover glass for protecting the inside is provided on an opening surface at the lower end portion of the microscope unit 412 (not illustrated).

A user such as an operator moves the microscope unit 412 or performs an imaging operation while operating various switches in the state of holding the microscope unit 412. Incidentally, preferably, the shape of the microscope unit 412 is long and elongated in the observation direction so that the user can easily change the viewing direction by grasping. For this reason, the shape of the microscope unit 412 may be a shape other than a column shape, for example, a polygonal column shape.

When the above-described imaging unit 32 is provided in the microscope unit 412 of the surgical microscope system 400 having the above-described configuration, even when the depth of field of the optical system itself is decreased by increasing the diaphragm diameter for higher image quality, it is possible to suppress the decrease in the apparent depth of field.

The embodiments for carrying out the present invention have been described above, but the present invention should not be limited only to the first to third embodiments. For example, in the first and second embodiments described above, in the description, the control device 5 performs signal processing and the like. However, the processing may be performed by the camera head 3 side. In the first and second embodiments, the rigid endoscope 2 is described as an example, but the present invention is also applicable to a flexible endoscope.

INDUSTRIAL APPLICABILITY

As described above, the imaging device according to the present invention is useful for suppressing a decrease in the depth of field even when the resolution is increased.

REFERENCE SIGNS LIST 1, 1A MEDICAL ENDOSCOPE SYSTEM
2 RIGID ENDOSCOPE

3 CAMERA HEAD
4, 4A, 5, 5A CONTROL DEVICE
6, 7 LIGHT GUIDE CABLE
8, 9 TRANSMISSION CABLE
10 DISPLAY DEVICE
21 INSERTION TUBE
22 FIRST CONDENSING OPTICAL SYSTEM
23 SECOND CONDENSING OPTICAL SYSTEM
31 OPTICAL PATH SEPARATION UNIT
32 IMAGING UNIT
41, 51 IMAGE PROCESSING UNIT
42, 52 LIGHT SOURCE UNIT
43, 53 INPUT UNIT
44 DISPLAY IMAGE GENERATION UNIT
45, 54 CONTROL UNIT
46, 55 STORAGE UNIT
47 FOCUS PROCESSING UNIT
48, 56 LENS DRIVE CONTROL UNIT
101 IMAGING DEVICE
311 TRIANGULAR PRISM
312, 313 MIRROR
314, 315 EYEPIECE OPTICAL SYSTEM
321 FIRST IMAGING UNIT
322 SECOND IMAGING UNIT
323 FIRST IMAGING OPTICAL SYSTEM
323a FIRST CONDENSING OPTICAL SYSTEM
323b FIRST TUBE LENS
324 FIRST IMAGE SENSOR
325 SECOND IMAGING OPTICAL SYSTEM
325a SECOND CONDENSING OPTICAL SYSTEM
325b SECOND TUBE LENS
326 SECOND IMAGE SENSOR
400 SURGICAL MICROSCOPE SYSTEM
410 MICROSCOPE DEVICE
411 DISPLAY DEVICE

The invention claimed is:

1. An imaging device comprising:
first and second image sensors that respectively capture a first optical image and a second optical image having parallax with each other;
a first imaging optical system that forms the first optical image on a light receiving surface of the first image sensor, the first imaging optical system including a first lens that is movable along a first optical axis direction;
a second imaging optical system that forms the second optical image on a light receiving surface of the second image sensor, the second imaging optical system including a second lens that is movable along a second optical axis direction, on condition that the first lens is at a first reference position along the first optical axis direction and the second lens is at a second reference position along the second optical axis direction, the first and second lenses are spaced apart along respective optical axis directions by a first deviation amount, and
focus processing circuitry configured to drive a focus mechanism to automatically adjust the first and second lenses relative to one another such that, on condition that at least one of the first and second lenses is moved closer to a corresponding image sensor relative to a corresponding reference position, the first and second lenses are spaced apart by a second deviation amount in respective optical axis directions, different from the first deviation amount, and, on condition that at least one of the first and second lenses is moved further from the corresponding image sensor relative to the corresponding reference position, the first and second lenses are spaced apart by a third deviation amount in respective optical axis directions is different from the first and second deviation amounts.

2. The imaging device according to claim 1, wherein the second deviation amount is larger than the third deviation amount.

3. The imaging device according to claim 2, wherein the focus mechanism includes a first drive to drive the first lens and second drive to drive the second lens, and
wherein the focus processing circuitry is configured to drive the first drive via a first drive controller, and drive the second drive via a second drive controller.

4. The imaging device according to claim 3, wherein the focus processing circuit is configured to determine positions of the first and second lenses based on an image captured by the first or second image sensor.

5. The imaging device according to claim 4, wherein the imaging device is mounted on a medical endoscope or a surgical microscope.

6. The imaging device according to claim 2, wherein the imaging device is mounted on a medical endoscope or a surgical microscope.

7. The imaging device according to claim 1, wherein the focus processing circuitry is configured to determine positions of the first and second lenses based on an image captured by the first or second image sensor.

8. The imaging device according to claim 7, wherein the second deviation amount is larger than the third deviation amount.

9. The imaging device according to claim 7, wherein the imaging device is mounted on a medical endoscope or a surgical microscope.

10. The imaging device according to claim 1, wherein the imaging device is mounted on a medical endoscope or a surgical microscope.

11. Focus processing circuitry for use with an imaging device including first and second image sensors that respectively capture a first optical image and a second optical image having parallax with each other, a first imaging optical system that forms the first optical image on a light receiving surface of the first image sensor, the first imaging optical system including a first lens that is movable along a first optical axis direction, and a second imaging optical system that forms the second optical image on a light receiving surface of the second image sensor, the second imaging optical s stem including a second lens that is movable along a second optical axis direction, on condition that the first lens is at a first reference position along the first optical axis direction and the second lens is at a second reference position along the second optical axis direction, the first and second lenses are spaced apart along respective optical axis directions by a first deviation amount, wherein the focus processing circuitry configured to
drive a focus mechanism to automatically adjust the first and second lenses relative to one another such that, on condition that at least one of the first and second lenses is moved closer to a corresponding image sensor relative to a corresponding reference position, the first and second lenses are spaced apart by a second deviation amount in respective optical axis directions, different from the first deviation amount, and, on condition that at least one of the first and second lenses is moved further from the corresponding image sensor relative to the corresponding reference position, the first and second lenses are spaced apart by a third deviation amount in respective optical axis directions is different from the first and second deviation amounts.

\* \* \* \* \*